United States Patent
Takahashi et al.

(10) Patent No.: US 10,159,457 B2
(45) Date of Patent: Dec. 25, 2018

(54) X-RAY DIAGNOSTIC APPARATUS

(71) Applicant: Canon Medical Systems Corporation, Otawara-shi (JP)

(72) Inventors: Akihito Takahashi, Nasushiobara (JP); Haruki Iwai, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/921,109

(22) Filed: Mar. 14, 2018

(65) Prior Publication Data
US 2018/0263587 A1 Sep. 20, 2018

(30) Foreign Application Priority Data
Mar. 15, 2017 (JP) .................. 2017-049482

(51) Int. Cl.
| | |
|---|---|
| *G06T 1/20* | (2006.01) |
| *A61B 6/00* | (2006.01) |
| *G01T 1/20* | (2006.01) |
| *H04N 5/32* | (2006.01) |

(52) U.S. Cl.
CPC .............. *A61B 6/5258* (2013.01); *A61B 6/40* (2013.01); *A61B 6/4233* (2013.01); *G01T 1/2018* (2013.01); *H04N 5/3205* (2013.01)

(58) Field of Classification Search
CPC ....... A61B 6/5258; A61B 6/40; A61B 6/4233; G01T 1/2018; H04N 5/3205
See application file for complete search history.

(56) References Cited

U.S. PATENT DOCUMENTS

| | | | |
|---|---|---|---|
| 7,742,560 B2* | 6/2010 | Spartiotis | A61B 6/14 250/370.09 |
| 2001/0038707 A1* | 11/2001 | Ohara | A61B 6/4233 382/132 |
| 2005/0243963 A1* | 11/2005 | Ghelmansarai | A61B 6/00 378/7 |
| 2007/0040124 A1* | 2/2007 | Accorsi | G01T 1/295 250/363.06 |
| 2007/0195931 A1 | 8/2007 | Ohishi | |
| 2007/0242802 A1* | 10/2007 | Dafni | A61B 6/4233 378/98.11 |
| 2013/0016809 A1* | 1/2013 | Suyama | G01N 23/04 378/57 |
| 2013/0108017 A1* | 5/2013 | Golubovic | G06T 7/0008 378/41 |
| 2014/0103220 A1 | 4/2014 | Ohta et al. | |
| 2015/0003584 A1 | 1/2015 | Weisfield et al. | |

(Continued)

FOREIGN PATENT DOCUMENTS

| | | |
|---|---|---|
| JP | 2007-215930 | 8/2007 |
| JP | 2008-167846 | 7/2008 |

(Continued)

*Primary Examiner* — Marcus Taningco
(74) *Attorney, Agent, or Firm* — Oblon, McClelland, Maier & Neustadt, L.L.P.

(57) ABSTRACT

An X-ray diagnostic apparatus comprises: an X-ray detector including a first detector and a second detector capable of simultaneously detecting X-rays irradiated from an X-ray tube; and processing circuitry configured to correct, by using information of a second image that is based on an output from the second detector, a first image that is based on an output from the first detector.

11 Claims, 7 Drawing Sheets

(56) References Cited

U.S. PATENT DOCUMENTS

| | | | | |
|---|---|---|---|---|
| 2015/0327825 A1* | 11/2015 | Suzuki | ............... | A61B 6/032 |
| | | | | 378/4 |
| 2016/0000396 A1* | 1/2016 | Taguchi | ............ | A61B 6/5205 |
| | | | | 378/5 |
| 2018/0172606 A1* | 6/2018 | Monkawa | ............ | G01N 23/04 |
| 2018/0211363 A1* | 7/2018 | Abe | ................ | G06T 3/4038 |

FOREIGN PATENT DOCUMENTS

| JP | 2015-80585 | 4/2015 |
|---|---|---|
| WO | WO 2013/015016 A1 | 1/2013 |

\* cited by examiner

X-RAY DIAGNOSTIC APPARATUS

CROSS-REFERENCE TO RELATED APPLICATIONS

This application is based upon and claims the benefit of priority from Japanese Patent Application No. 2017-49482, filed on Mar. 15, 2017; the entire contents of which are incorporated herein by reference.

FIELD

Embodiments described herein relate generally to an X-ray diagnostic apparatus.

BACKGROUND

Conventionally, during medical examinations using X-ray diagnostic apparatuses, a small region of interest may be observed with a high resolution in some situations. For this reason, a known X-ray diagnostic apparatus is provided with detectors including both a first detector that has a large field of view (FOV) part using a Thin Film Transistor (TFT) array and a second detector that uses a Complementary Metal Oxide Semiconductor (CMOS) and has a smaller FOV and a smaller pixel pitch than those of the first detector.

With such a type of X-ray diagnostic apparatus, a technique is known by which the detector in use is switched between the first detector and the second detector depending on purposes, so as to display one selected from between a first image generated from an X-ray signal output by the first detector and a second image generated from an X-ray signal output by the second detector.

DETAILED DESCRIPTION

An X-ray diagnostic apparatus comprises an X-ray detector and processing circuitry. The X-ray detector includes a first detector and a second detector capable of simultaneously detecting X-rays irradiated from an X-ray tube. The processing circuitry is configured to correct, by using information of a second image that is based on an output from the second detector, a first image that is based on an output from the first detector.

Exemplary embodiments of the X-ray diagnostic apparatus will be explained below, with reference to the drawings. Embodiments are not limited to the embodiments described below. Further, the contents of each of the embodiments are, in principle, similarly applicable to any other embodiment.

Figure 1:
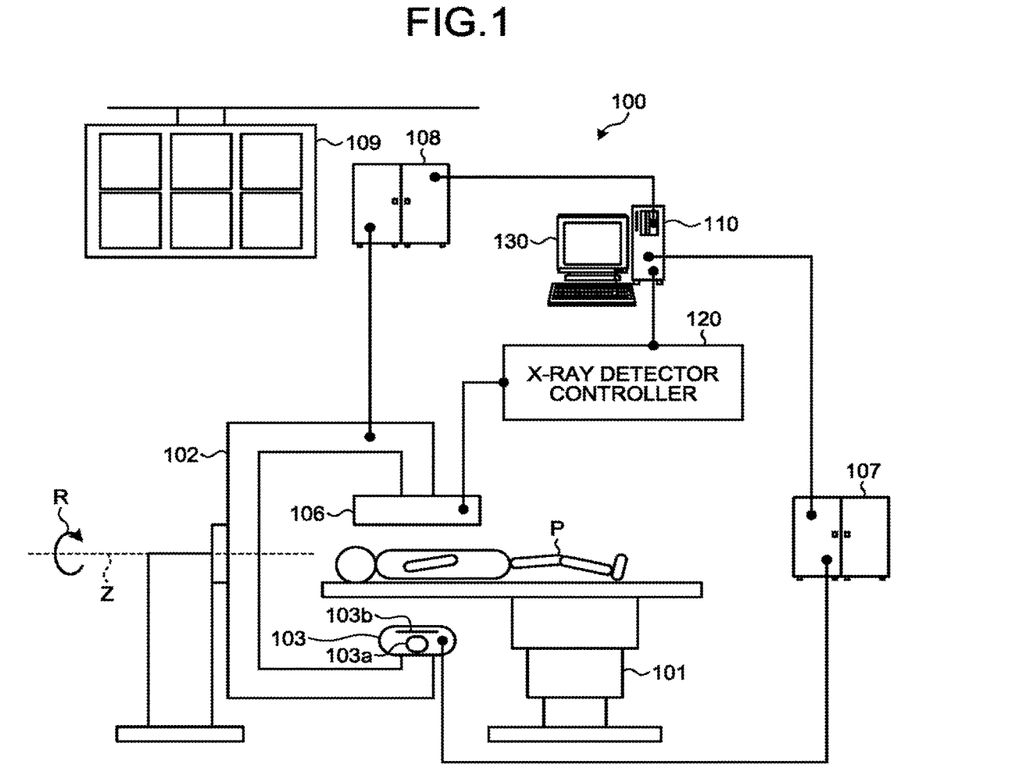
FIG. 1 is a block diagram illustrating an exemplary configuration of an X-ray diagnostic apparatus according to a first embodiment.

FIG. 1 is a block diagram illustrating an exemplary configuration of an X-ray diagnostic apparatus 100 according to a first embodiment. As illustrated in FIG. 1, the X-ray diagnostic apparatus 100 according to the first embodiment includes a catheter bed 101, a holder 102, an X-ray high-voltage generator 107, a holder controller 108, a monitor 109, an X-ray image acquirer 110, an X-ray detector (Flat Panel Detector) controller 120, and an input interface 130.

The catheter bed 101 is movable in a vertical direction and a horizontal direction. A subject P is placed on the catheter bed 101. The holder 102 is configured to be rotatable on a Z-axis in the direction indicated with the arrow R and is configured to hold an X-ray source 103 and an X-ray detector 106 facing each other.

The X-ray source 103 includes an X-ray tube 103a configured to irradiate X-rays and an aperture (also referred to as a collimator) and radiation quality adjusting filter 103b used for the purpose of reducing the radiation exposure amount for the subject P and improving image quality of image data.

Figure 2:
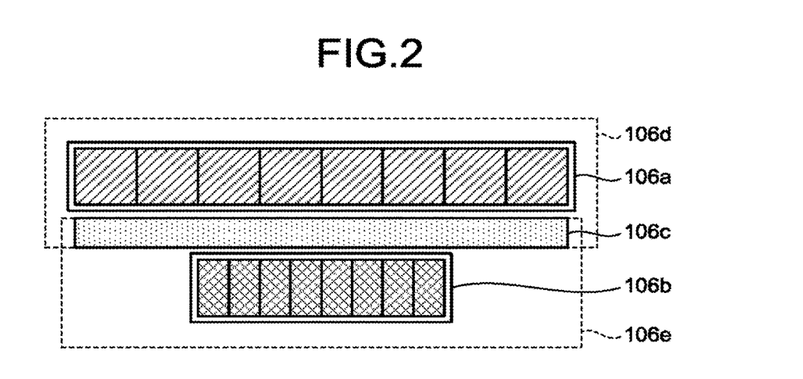
FIG. 2 is a block diagram illustrating an exemplary configuration of an X-ray detector according to the first embodiment.

The X-ray detector (which may be referred to as a Flat Panel Detector [FPD]) 106 is configured to detect X-rays that were irradiated from the X-ray source 103 and have passed through the subject P. The X-ray detector 106 includes a first detector and a second detector that are capable of simultaneously detecting X-rays irradiated from the X-ray source 103. In the following sections, the X-ray detector 106 according to the first embodiment will be explained, with reference to FIG. 2. FIG. 2 is a block diagram illustrating an exemplary configuration of the X-ray detector 106 according to the first embodiment.

For example, as illustrated in FIG. 2, the X-ray detector 106 includes a first photodetector 106a, a second photodetector 106b, and a scintillator 106c. The first photodetector 106a and the scintillator 106c constitute a first detector 106d (also referred to as a first FPD), and the second photodetector 106b and the scintillator 106c constitute a second detector 106e (also referred to as a second FED). The first FED is one example of the first detector. The second FED is one example of the second detector. In FIG. 2, the scintillator 106c is arranged so as to be sandwiched between the first photodetector 106a and the second photodetector 106b.

The scintillator 106c is configured to convert the F-rays irradiated from the X-ray source 103 into light. The first photodetector 106a includes a two-dimensional image sensor using a Thin Film Transistor (TFT) array formed by using amorphous silicon, for example, and is configured to detect the light converted from X-rays by the scintillator 106c and to output an electrical signal. The second photodetector 106b includes a two-dimensional image sensor using a Complementary Metal Oxide Semiconductor (CMOS) transistor, for example, and is configured to detect the light converted from X-rays by the scintillator 106c and to output an electrical signal. The electrical signals output by the first photodetector 106a and the second photodetector 106b may be referred to as X-ray signals.

In this manner, the scintillator 106c is shared by the first photodetector 106a and the second photodetector 106b. In other words, the X-ray detector 106 includes: the scintillator 106c configured to convert the X-rays irradiated from the X-ray source 103 into the light; and the first photodetector 106a and the second photodetector 106b that share the scintillator 106c and are configured to detect the light converted by the scintillator 106c and to output the electrical signals. Further, the first photodetector 106a and the second photodetector 106b are configured to output the electrical signals as a result of simultaneously detecting the light converted from X-rays by the scintillator 106c.

Further, as illustrated in FIG. 2, the first photodetector 106a and the second photodetector 106b each include a plurality of elements serving as structural units of pixels. Each of the elements is configured to convert a fluorescent image obtained as a result of incidence of an X-ray, into an electrical signal and to store the electrical signal into a photodiode (PD). FIG. 2 illustrates an example in which the first photodetector 106a includes eight elements, and the second photodetector 106b includes eight elements.

In this situation, the pixel pitch of the elements of the second photodetector 106b is smaller than the pixel pitch of the elements of the first photodetector 106a. In the example illustrated in FIG. 2, the pixel pitch of the elements of the first photodetector 106a corresponds to the pixel pitch of two elements of the second photodetector 106b. In other words, the resolution of the second photodetector 106b is higher than that of the first photodetector 106a. Further, as illustrated in FIG. 2, the size of the FOV of the first photodetector 106a is larger than that of the second photodetector 106b.

Further, the maximum incident X-ray amount of the second photodetector 106b using the CMOS tends to be smaller than that of the first photodetector 106a using amorphous silicon. For this reason, with the second photodetector 106b, when an attempt is made to acquire X-ray image data having a high Signal-to-Noise (S/N) ratio by radiating X-rays of a high dose, it may not be possible to do so in some situations.

Further, a residual component resulting from incident X-ray of the second photodetector 106b is smaller than that of the first photodetector 106a. In the first photodetector 106a, within the photodiodes, generated electric charges are trapped at a trap level on the inside thereof. In contrast, in the second photodetector 106b, due to the nature of the CMOS, not many of the electric charges generated in the photodiodes are trapped. In other words, an electrical signal residual component of the second optical detector 106b is smaller than that of the first optical detector 106a.

Returning to the description of FIG. 1, the X-ray detector controller 120 is configured to control timing with which the electrical signals are read by the X-ray detector 106. Further, the X-ray detector controller 120 is configured to acquire the electrical signals from the X-ray detector 106, to generate image data from the acquired electrical signals, and to output the image data to the X-ray image acquirer 110. In this situation, the X-ray detector controller 120 acquires the electrical signal output by the first FPD, generates first image data (which may be referred to as a first FPD image or a first image) from the acquired electrical signal, and outputs the first image data to the X-ray image acquirer 110. Further, the X-ray detector controller 120 acquires the electrical signal output by the second FPD, generates second image data (which may be referred to as a second FPD image or a second image) from the acquired electrical signal, and outputs the second image data to the X-ray image acquirer 110.

The X-ray image acquirer 110 is configured to acquire the image data output by the X-ray detector controller 120 by controlling the holder controller 108 and the X-ray high-voltage generator 107 and to further perform an image processing process. In this situation, the X-ray image acquirer 110 acquires the image data from the first FPD and from the second F0D, with substantially the same timing. Details of the X-ray image acquirer 110 will be explained later.

The X-ray high-voltage generator 107 is configured to supply high voltage to the X-ray tube 103a. Under the control of the X-ray image acquirer 110, the holder controller 108 is configured to control rotations of the holder 102, and the like. The monitor 109 is configured to display an X-ray image generated by the X-ray image acquirer 110 and the like. The monitor 109 may be structured with a plurality of sub monitors or may be a large-screen monitor capable of arbitrarily dividing the display region thereof according to an instruction from the operator. Further, when the monitor 109 includes the plurality of sub monitors, the display region of each of the sub monitors may arbitrarily be divided according to an instruction from the operator. The input interface 130 is configured by using a keyboard, a control panel, a foot switch, and/or the like and is configured to receive inputs of various types of operations performed on the X-ray diagnostic apparatus 100 from the operator.

An overall configuration of the X-ray diagnostic apparatus 100 according to the first embodiment has thus been explained. Structured as described above, the X-ray diagnostic apparatus 100 according to the first embodiment is configured to acquire the X-ray signals output by the X-ray detector 106. Further, the X-ray diagnostic apparatus 100 is configured to cause the monitor 109 to display an image generated from the acquired X-ray signals. For example, the X-ray diagnostic apparatus 100 causes the monitor 109 to display an image set by the operator in accordance with a clinical site. For example, the X-ray diagnostic apparatus 100 causes the monitor 109 to display images by switching between the first image and the second image according to an instruction from the operator.

Figure 3:
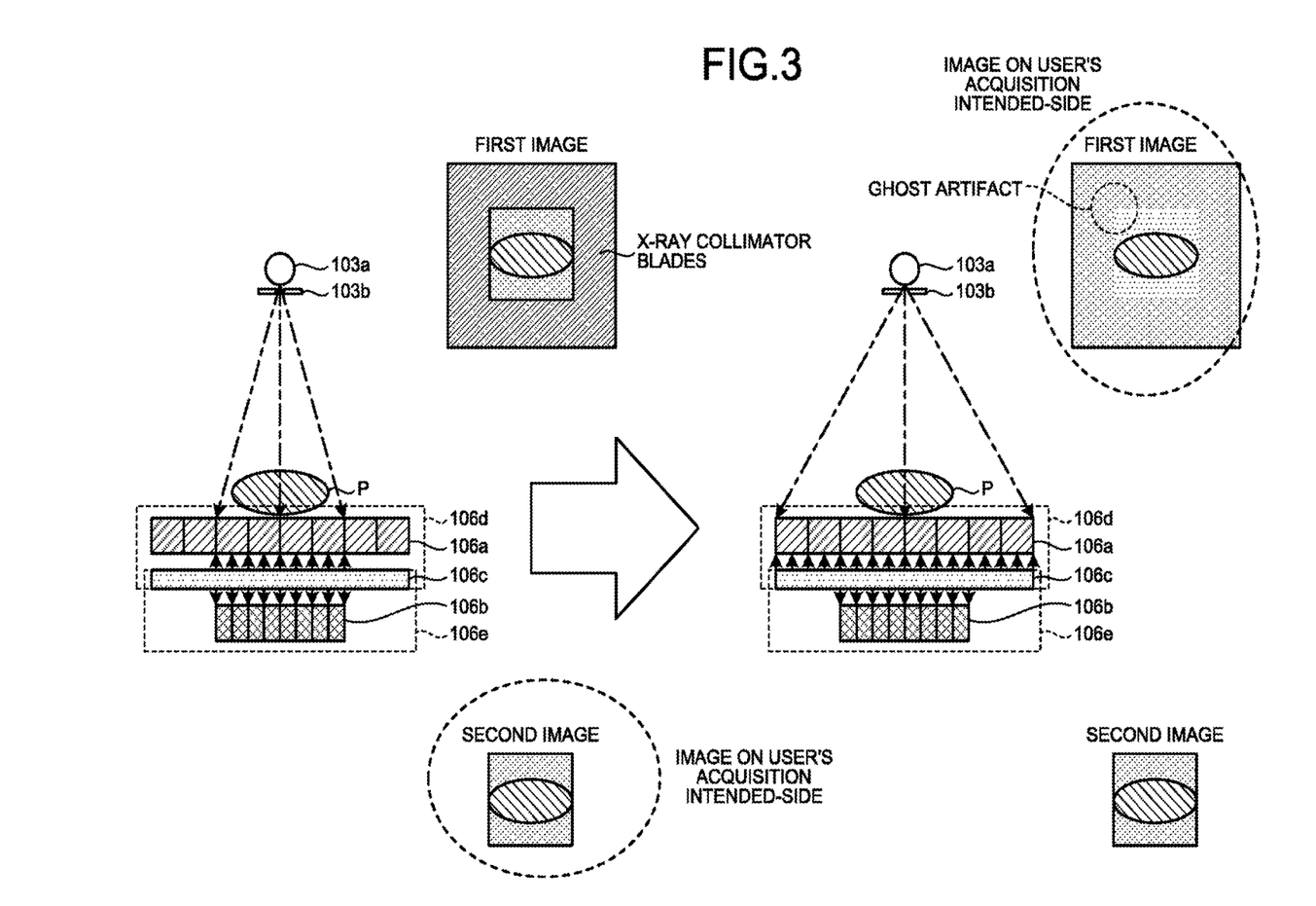
FIG. 3 is a diagram for explaining operations in an X-ray image acquiring process performed by a conventional X-ray diagnostic apparatus.

In such an X-ray diagnostic apparatus, in some situations, the second FPD that is on the second photodetector 106b side and has a higher resolution and a smaller FOV may be used during a treatment manipulation or the like, for a relatively long period of time. FIG. 3 is a diagram for explaining operations in an X-ray image acquiring process performed by a conventional X-ray diagnostic apparatus 100.

The left section of FIG. 3 illustrates an example in which an X-ray radiation region is set to be equal to the size of the FOV of the second FPD. In that situation, the X-ray diagnostic apparatus 100 acquires the X-ray signal output by the second FPD and causes the monitor 109 to display the second image as an image on the user's acquisition intended-side. In this situation also, the X-ray diagnostic apparatus 100 acquires the X-ray signal output by the first FPD and generates the first image. Rendered in the first image are a FOV having an equal size to the size of the FOV of the second FPD and X-ray collimator blades in the surroundings of the FOV.

Subsequently, the image displayed on the monitor 109 is changed from the second image to the first image. The right section of FIG. 3 illustrates an example in which the X-ray radiation region is changed to have the size of the FOV of the first FPD. In that situation, the X-ray diagnostic apparatus 100 acquires the X-ray signal output by the first FPD and causes the monitor 109 to display the first images an image on the user's acquisition intended-side. In this situation also, the X-ray diagnostic apparatus 100 acquires the X-ray signal output by the second FPD and generates the second image. Rendered in the second image is a FOV having an equal size to the size of the FOV of the second FPD.

In this situation, for example, when a fluoroscopy/imaging manipulation is performed by using the second FPD for a long period time, in the region of the first FPD corresponding to the size of the FOV of the second FPD, offset components of the image are changed, due to the generated electric charges trapped at the trap level being read with timing different from expected timing. This change in the offset components is caused because, when powerful X-rays have been irradiated onto the first FPD for a certain period of time, the generated electric charges are trapped at the trap level on the inside of the photodiodes configured to detect the light, and the electric charges are released by energy of heat or the like and are read as being mixed with subsequent X-ray signals. In other words, in the first FPD, the electric charges are read as being mixed with the X-ray signals, with undesirable timing. For this reason, in a fluoroscopic image having a larger FOV obtained the first FPD after using the second FPD for a long period of time, an artifact exhibiting something like a baked pattern occurs, due to an electrical signal residual component of the first photodetector 106a. This artifact may appear approximately 10 seconds, for example. In contrast, no such artifact appears on the outside of the size of the FOV of the second FPD to which incidence of X-rays is blocked by the aperture blades of the X-ray collimator.

Accordingly, when the first FPD, which is on the first photodetector 106a side, that has a larger FOV is selected for the subsequent manipulation, an image is obtained in which a pattern is baked in accordance with the difference in the radiation history on the first FPD made by the X-ray collimator. For example, in some situations, a fluoroscopic image obtained by the first FPD may exhibit a pattern in which the shapes of the blades of the X-ray collimator are baked. The first image illustrated in the upper right section of FIG. 3 indicates that, when an image acquisition is performed by using the second FPD, and subsequently another image acquisition is performed by switching to the first FPD, an artifact having the shapes of the blades of the X-ray collimator is exhibited. The baked pattern in the first image described above occurring due to the electrical signal residual component will hereinafter be referred to as a ghost artifact. In other words, the ghost artifact occurs due to the electrical signal residual component of the first photodetector 106a.

In the CMOS, due to the nature thereof, not many of the electric charges generated in the photodiodes are trapped. Accordingly, ghost artifacts are much less likely to occur in the CMOS, compared to those in the amorphous silicon TFT used in the first FPD. For this reason, when correcting the region of the first FPD image corresponding to the FOV of the second FPD, it is acceptable to refer to the second FPD image, which is free of changes made by an X-ray dose history.

For this reason, when causing the monitor 109 to display the first image generated from the electrical signal output by the first photodetector 106a, the X-ray diagnostic apparatus 100 according to the first embodiment corrects first image by using information of the second image generated from the electrical signal output by the second photodetector 106b. This correcting process is performed by the X-ray image acquirer 110. In the following sections, details of the correcting process performed by the X-ray image acquirer 110 will be explained, with reference to FIG. 4. The X-ray image acquirer 110 is an example of a controller.

Figure 4:
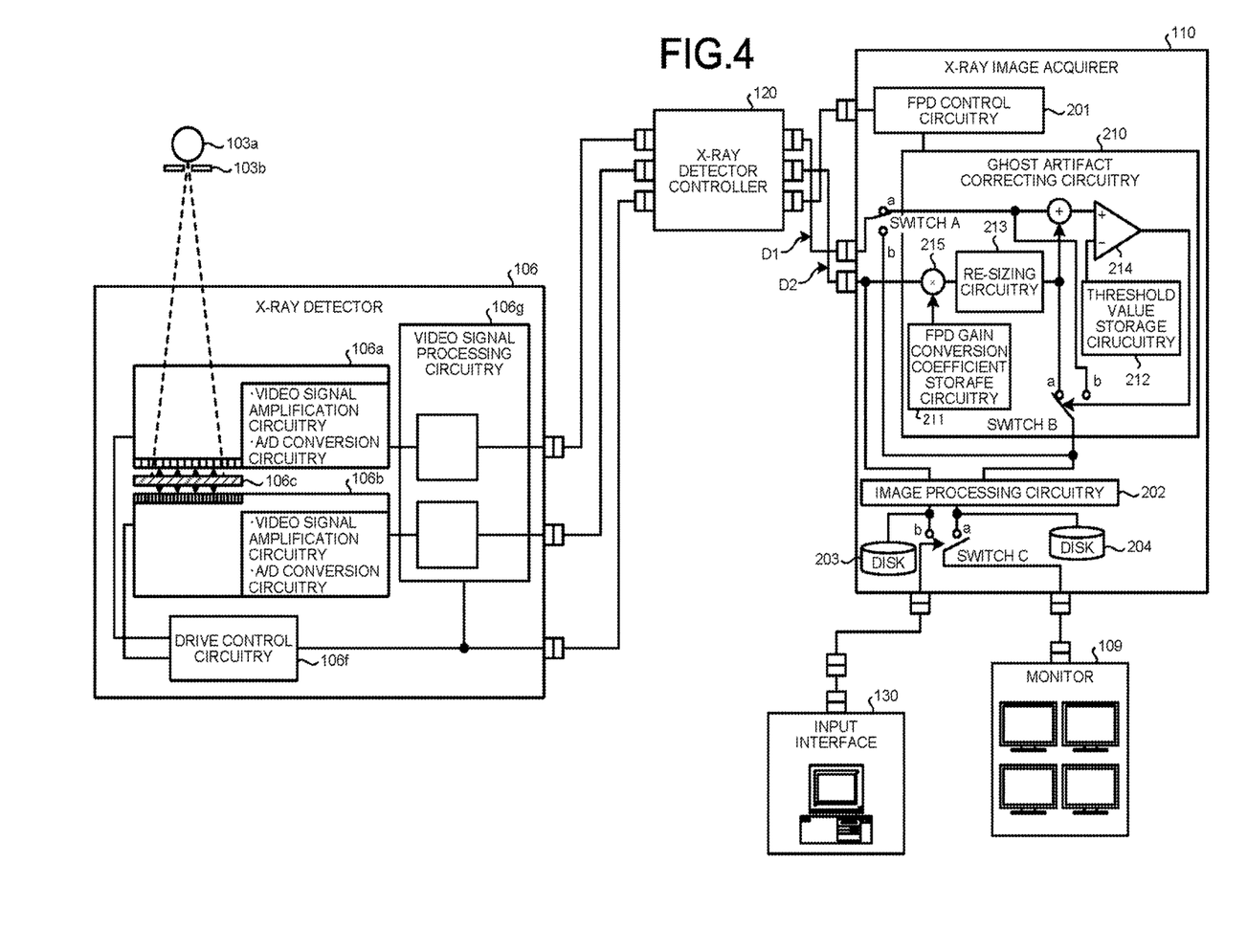
FIG. 4 is a block diagram illustrating an exemplary configuration of an X-ray image acquirer according to the first embodiment.

FIG. 4 is a block diagram illustrating an exemplary configuration of the X-ray image acquirer 110 according to the first embodiment. For convenience of explanation, FIG. 4 also illustrates the X-ray source 103, the X-ray detector 100, the X-ray detector controller 120, the monitor 109, and the input interface 130. FIG. 2 illustrates the example in which the X-ray detector 106 includes the first photodetector 106a, the second photodetector 106b, and the scintillator 106c. However, in actuality, as illustrated in FIG. 4, the X-ray detector 106 also includes video signal amplification circuitry and analog to digital (A/D) conversion circuitry. The second photodetector 106b may be configured so that each of the elements includes A/D conversion circuitry and video signal amplification circuitry. In that situation, the second photodetector 106b is configured to convert a stored electrical signal into a digital signal, to subsequently amplify the digital signal, and to output the amplified digital signal. With this arrangement, the second photodetector 106b is able to output the electrical signal in which noise is decreased. As illustrated in FIG. 4, in the X-ray detector 106, the first FPD is provided on the X-ray source 103 side, relative to the second FPD.

Further, the X-ray detector 106 includes drive control circuitry 106f and video signal processing circuitry 106g. The drive control circuitry 106f is configured to control driving timing of the first photodetector 106a and the second photodetector 106b under the control of the X-ray detector controller 120. The video signal processing circuitry 106g is configured to acquire an electrical signal output from the first photodetector 106a, to output the acquired electrical signal to the X-ray detector controller 120, to acquire an electrical signal output from the second photodetector 106b, and to output the acquired electrical signal to the X-ray detector controller 120.

With reference to FIG. 4, the example is explained in which the transfer of images from the X-ray detector controller 120 to the X-ray image acquirer 110 uses a parallel scheme where data lines are provided for the first image and for the second image; however, embodiments are not limited to this example For instance, the transfer of the images from the X-ray detector controller 120 to the X-ray image acquirer 110 may use a serial scheme where a data line is shared between the first image and the second image.

The X-ray image acquirer 110 according to the first embodiment includes, as illustrated in FIG. 4, FPC control circuitry 201, image processing circuitry 202, a disk 203, a disk 204, and ghost artifact correcting circuitry 210.

The FFD control circuitry 201 is configured to control, via the X-ray detector controller 120, timing with which the electrical signals are read by the X-ray detector 106. The image processing circuitry 202 is configured to perform an image processing process on the image data output by the X-ray detector controller 120. The disk 203 is configured to store X-ray images therein. For example, the disk 203 is configured with a Hard Disk Drive (HDD) and stores the second image therein. The disk 204 is configured to store X-ray images therein. For example, the disk 204 is configured with an HDD and stores the first image therein. The input interface 130 is configured to receive an instruction from the operator and to control a switch C. In this situation, when the input interface 130 moves the switch C to side "a", the image processing circuitry 202 displays the first image. In contrast, when the input interface 130 moves the switch C to side "b", the image processing circuits 202 displays the second image. With reference to FIG. 4, the example is explained in which the X-ray image acquirer 110 includes the disk 203 for the second image and the disk 204 for the first image; however, another arrangement is also acceptable in which the first image and the second image share a single disk.

The ghost artifact correcting circuitry 220 is configured to determine whether a ghost artifact has occurred or not. For example, the ghost artifact correcting circuitry 210 calculates the difference value between a pixel value obtained by multiplying a pixel value of the second image by a coefficient corresponding to a sensitivity ratio between the first photodetector 106a and the second photodetector 106b and a pixel value of the first image and, when the calculated difference value is equal to or larger than a set threshold value, the ghost artifact correcting circuitry 210 determines that a ghost artifact has occurred. In this situation, the ghost artifact correcting circuitry 210 performs the determining process described below, on ice pixels in a FOV region of the first FPD corresponding to the size of the FOV of the second FPD. In that situation, in the X-ray image acquirer 110, a switch A illustrated in FIG. 4 is moved to side "a", so that the pi in the FOV region of the first FPD corresponding to the size of the FOV of the second FPD are input to the ghost artifact correcting circuitry 210. After that, the ghost artifact correcting circuitry 210 performs the determining process. Further, in the X-ray image acquirer 110, when the processed region of the first FOP image is out of the size of the FOV of the second FPD, the switch A is moved to side "b", so that the original first FPD image is input to the image processing circuitry 202 without going through the determining process. The ghost artifact correcting circuitry 210 includes, for example, FPD gain conversion coefficient storage circuitry 211, threshold value storage circuitry 212, re-sizing circuitry 213, determining circuitry 214, and multiplying circuitry 215.

The FPD gain conversion coefficient storage circuitry 211 is configured to store therein the coefficient corresponding to the sensitivity ratio between the first photodetector 106a and the second photodetector 106b. The threshold value storage circuitry 212 is configured to store therein the threshold value used by the determining circuitry 214.

The multiplying circuitry 215 is configured to read the coefficient stored in the FPD gain conversion coefficient storage circuitry 211 and to multiply the second image by the read coefficient. By multiplying the second FOD image, which is free of changes made by an X-ray dose history, by the coefficient corresponding to the sensitivity ratio between the first photodetector 106a and the second photodetector 106b, the multiplying circuitry 215 calculates pixel values of the first FPD image in a state that is free of changes in the X-ray dose history. The multiplying circuitry 215 then forwards the second image after the multiplication, to the re-sizing circuitry 213.

When the pixel value of the first image is compared with the pixel value of the second image, the re-sizing circuitry 213 is configured to correct the pixel pitch of the second image. The second FPD has a smaller pixel pitch and a higher resolution than the first FPD. For this reason, to compare pixel values in the same position between the first image and the second image, the re-sizing circuitry 213 makes a correction so that the pixel pitch of the second FPD image becomes equal to the pixel pitch of the first FPD image. The re-sizing circuitry 213 forwards the second image after the re-sizing process, to the determining circuitry 214.

The determining circuitry 214 is configured to calculate the difference value between the pixel value obtained by multiplying the pixel value of the second image by the coefficient corresponding to the sensitivity ratio between the first photodetector 106a and the second photodetector 106b and the pixel value of the first image and determines whether or not the difference value is larger than the set threshold value. In other words, the determining circuitry 214 calculates the difference value between the pixel value of the first FPD image in a state that is free of changes in the X-ray dose history and the actual pixel value of the first FPD image and determines whether or not the calculated difference value is larger than the set threshold value. Further, when the difference between the pixel value obtained by multiplying the pixel value of the second image by the coefficient corresponding to the sensitivity ratio between the first photodetector 106a and the second photodetector 106b and the pixel value of the first image is equal to or larger than the threshold value, the determining circuitry 214 determines that an artifact has occurred. In that situation, the switch B is moved to side "a", so that the pixel value obtained from the second FPD image replaces the pixel value obtained from the first FPD image and is input to the image processing circuitry 202.

The image processing circuitry 202 is configured to separately apply necessary image processing processes to the first FPD image and to store the first FPD image into the disk 204, and to also cause the monitor 109 to display the first FPD image. In this situation, because the first FPD image is designated by the user through the input interface 130, as an image currently desired by the user to be displayed, the switch C is moved to side "a". In contrast, when a manipulation using the second FPD is selected by the user through the input interface 130, the image processing circuitry 202 causes the monitor 109 to display the second FPD image. In that situation, the switch C is moved to side "b". In the present embodiment, the example is explained in which the ghost artifact is exhibited as the blades of the X-ray collimator; however, embodiments are not limited to this example. Further, as long as the positions of the blades of the X-ray collimator are within the size of the FOV of the second FPD, it is possible to similarly correct ghost artifacts of the blades.

Figure 5:
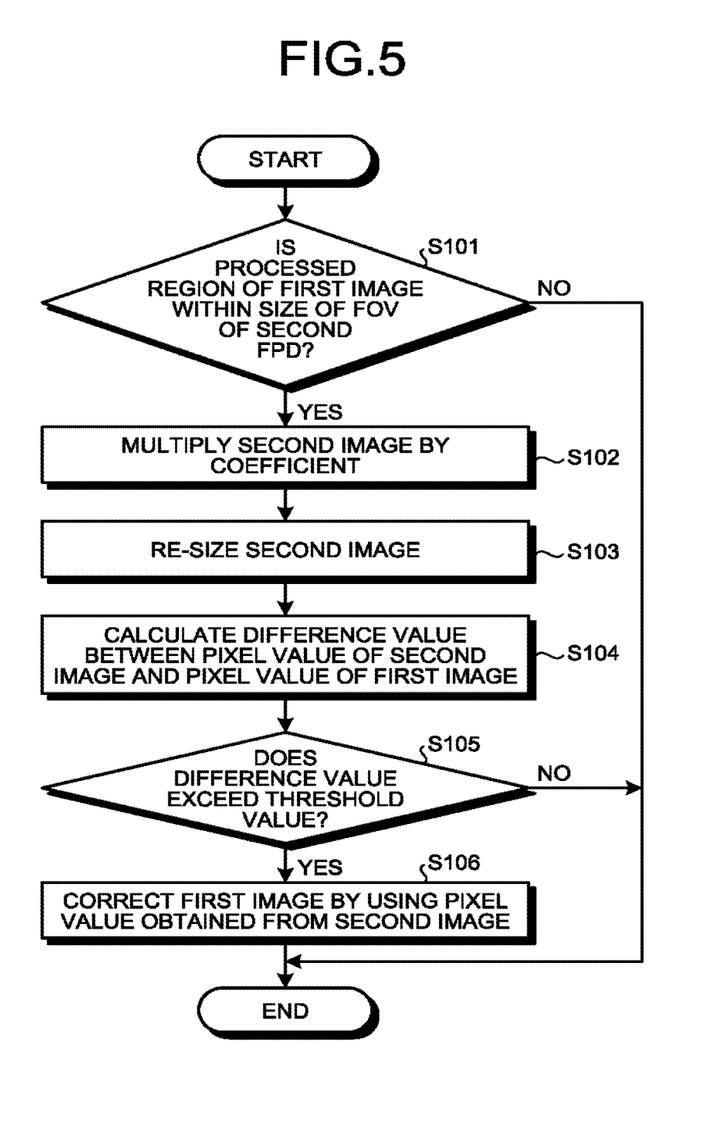
FIG. 5 is a flowchart illustrating a processing procedure performed by the X-ray image acquirer according to the first embodiment.

FIG. 5 is a flowchart illustrating a processing procedure performed by the X-ray image acquirer 110 according to the first embodiment. FIG. 5 presents the flowchart explaining overall operations of the X-ray image acquirer 110, and the following sections will explain to which steps in the flowchart, the constituent elements thereof correspond. The following explanation is based on the assumption that the processes illustrated in FIG. 5 are performed in real time when a change to the first image is received at the time of acquiring the second image.

Step S101 is a step implemented by the X-ray image acquirer 110. At step S101, the X-ray image acquirer 110 determines whether or not the processed region of the first image is within the size of the FOV of the second FPD. In this situation, when it is determined that the processed region of the first image is not within the size of the FOV of the second FPD (step S101: No), the X-ray image acquirer 110 ends the process. On the contrary, when it is determined that the processed region of the first image is within the size of the FOV of the second FPD (step S101: Yes), the X-ray image acquirer 110 proceeds to step S102.

Step S102 is a step implemented by the multiplying circuitry 215 included in the ghost artifact correcting circuitry 210. At step S102, the multiplying circuitry 215 multiplies the second image by the coefficient.

Step S103 is a step implemented by the re-sizing circuitry 213 included in the ghost artifact correcting circuitry 210. At step S103, the re-sizing circuitry re-sizes the second image. In other words, the re-sizing circuitry 213 enlarges the second image so as to arrange the pixel pitch of the second image to be equal to the pixel pitch of the first image.

Step S104 is a step implemented by the determining circuitry 214 included in the ghost artifact correcting circuitry 210. At step S104, the determining circuitry 214 calculates the difference value between the pixel value of the second image and the pixel value of the first image.

Step S105 is a step implemented by the determining circuitry 214 included in the ghost artifact correcting circuitry 210. At step S105, the determining circuitry 214 determines whether or not the difference value exceeds the threshold value. In this situation, when it is determined that the difference value does not exceed the threshold value (step S105: No), the determining circuitry 214 ends the process. On the contrary, when it is determined that the difference value exceeds the threshold value (step S105: Yes), the determining circuitry 214 proceeds to step S106.

Step S106 is a step implemented by the image processing circuitry 202 included in the X-ray image acquirer 110. At step S106, the image processing circuitry 202 corrects the first image by using the pixel value obtained from the second image.

As explained above, in the first embodiment, the electrical signal residual component of the second photodetector 106b is smaller than that of the first photodetector 106a. In other words, no artifact due to the electrical signal residual component is caused in the second photodetector 106b. Further, in the first embodiment, in the situation where an artifact due to an electrical signal residual component occurs in the first image, when the image displayed on the monitor 109 is changed from the second image to the first image, the X-ray image acquirer 110 corrects the first image by using the pixel value obtained from the second image. As a result, according to the first embodiment, for example, it is possible to provide an image free of the occurrence of ghost artifacts.

In the first embodiment above, the example is explained in which the second photodetector 106b includes the two-dimensional image sensor using the CMOS transistor; however, embodiments are not limited to this example. For instance, as the image sensor of the second photodetector 106b, it is acceptable to use amorphous silicon having a characteristic where fewer electric charges generated in the photodiode are trapped.

In the first embodiment above, the example is explained in which the correction is made by replacing the pixel value obtained from the first FPD image with the pixel value obtained from the second FPD image; however, embodiments are not limited to this example. For instance, it is also acceptable to correct the pixel value obtained from the first FPD image by using a correction value based on the pixel value obtained from the second FPD image. In that situation, the first FPD image and the second FPD image are input to the image processing circuitry 202. In this situation, when an artifact occurs in the first FFD image, the pixel value of the second FPD image input to the image processing circuitry 202 corresponds to the pixel value of the first FFD image without the occurrence of artifacts. Accordingly, the image processing circuitry 202 calculates a correction value based on the pixel value of the second FPD image and the pixel value of the first FPD image. For instance, the image processing circuitry 202 corrects at least one of the pixel value of the second FPD image and the pixel value of the first FPD image corresponding to sensitivity of the first photodetector 106a and the second photodetector 106b. And the image processing circuitry 202 calculates a value obtained by subtracting a pixel value of the corrected first FPD image from a pixel value of the corrected second FPD image, as a correction value. After that, the image processing circuitry 202 corrects the first FPD image by subtracting the calculated correction value from the pixel value of the first FPD image. Thus, the image processing circuitry 202 corrects residual component of the first image.

In the first embodiment, the example is explained in which, in the situation where an artifact due to an electrical signal residual component occurs in the first image, when the image displayed on the monitor 109 is changed from the second image to the first image, the first image is corrected by using the pixel value obtained from the second image. Incidentally, the X-ray diagnostic apparatus 100 may, in some situations, carry out a Digital Subtraction Angiography (DSA) imaging process with a FOV slightly larger than the second FPD, by using the first PD.

Figure 6A:
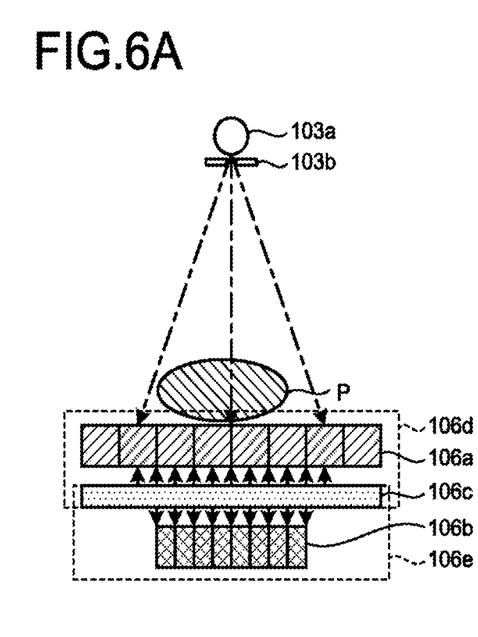
FIG. 6A is a diagram for explaining a second embodiment.
Figure 6B:
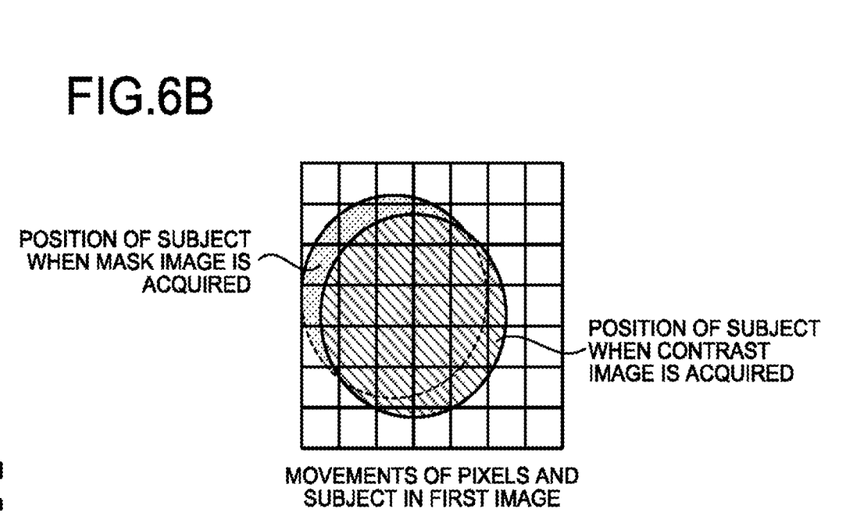
FIG. 6B is another diagram for explaining the second embodiment.
Figure 6C:
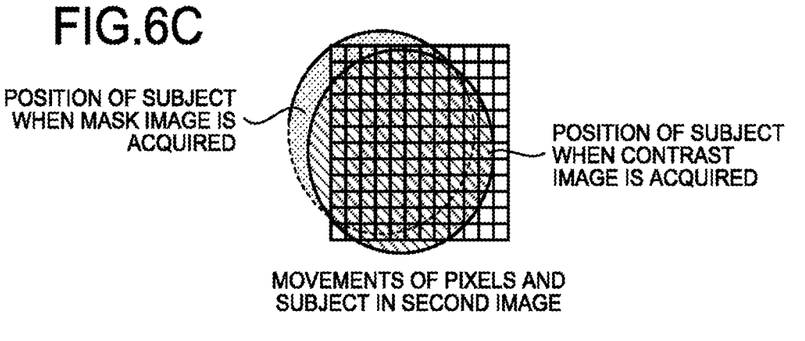
FIG. 6C is yet another diagram for explaining the second embodiment.

In that situation, when a motion artifact occurs due to a movement of the subject between the time of acquiring a mask image and the time of acquiring a contrast image during the DSA manipulation, the corresponding pixels shift between the mask image and the contrast image. FIGS. 6A, 6B, and 6C are diagrams for explaining a second embodiment.

FIGS. 6A, 6B, and 6C illustrate an example in which the first FPD image was designated by the user through the input interface 130, and the operator has performed DSA manipulations while looking at the first image. FIG. 6A illustrates the X-ray source 103 and the X-ray detector 106. In that situation, the first FPD and the second FPD each output an electrical signal.

FIG. 6B illustrates a mask image and a contrast image generated from the electrical signal output by the first FED. In this situation, when a pixel shift amount between the mask image and the contrast image is calculated, it may not be possible to achieve a sufficient level of precision for the correction in some situations, because the size of each pixel to be used is too large.

In this regard, as illustrated in FIG. 6C, when the pixel shift amount between the mask image and the contrast image is calculated, by using the second image having a smaller pixel size, it is possible to accurately measure the shift between the mask image and the contrast image. It is therefore possible to calculate the pixel shift amount more accurately. Accordingly, in the second embodiment, an example will be explained in which, when the DSA manipulations have been performed while the first FPD image is designated, a motion artifact occurring between the mask image and the contrast image is corrected by using the second FED image.

Figure 7:
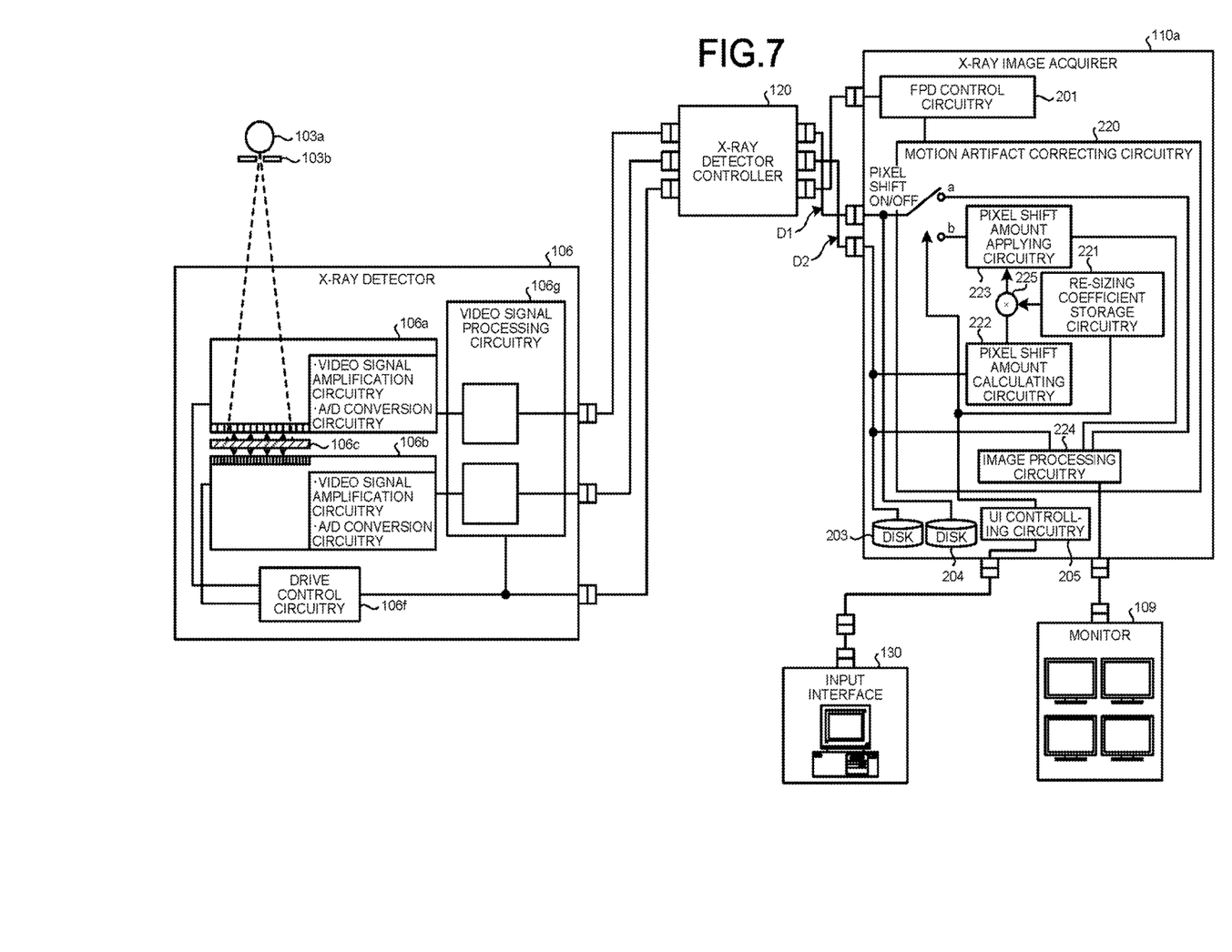
FIG. 7 is a block diagram illustrating an exemplary configuration of an X-ray image acquirer according to the second embodiment.

Except that an X-ray image acquirer 110a has functions different from those of the X-ray image acquirer 110 according to the first embodiment, an overall configuration of the X-ray diagnostic apparatus 100 according to the second embodiment is the same as the exemplary configuration illustrated in FIG. 1. Thus, explanation thereof will be omitted. The X-ray image acquirer 110a is an example of controller. FIG. 7 is a block diagram illustrating an exemplary configuration of the X-ray image acquirer 110a according to the second embodiment. For convenience of explanation, FIG. 7 also illustrates the X-ray source 103, the X-ray detector 106, the X-ray detector controller 120, the monitor 109, and the input interface 130. As illustrated in FIG. 7, in the X-ray detector 106, the first FPD is provided on the X-ray source 103 side, relative to the second FPD.

With reference to FIG. 7, the example is explained in which the transfer of images from the X-ray detector controller 120 to the X-ray image acquirer 110a uses a parallel scheme where data lines are provided for the first image and for the second image; however, embodiments are not limited to this example. For instance, the transfer of the images from the X-ray detector controller 120 to the X-ray image acquirer 110a may use a serial scheme where a data line is shared between the first image and the second image.

The X-ray image acquirer 110a according to the second embodiment includes, as illustrated in FIG. 7, the FPD control circuitry 201, the disk 203, the disk 204, UI controlling circuitry 205, and motion artifact correcting circuitry 220.

The FPD control circuitry 201 is configured to control, via the X-ray detector controller 120, timing with which the electrical signals are read by the X-ray detector 106. The disk 203 is configured to store X-ray images therein. For example, the disk 203 is configured with an HOD and stores the second image therein. The disk 204 is configured to store X-ray images therein. For example, the disk 204 is configured with an HDD and stores the first image therein. With reference to FIG. 7, the example is explained in which the X-ray image acquirer 110a includes the disk 203 for the second image and the disk 204 for the first image; however, another arrangement is also acceptable in which the first image and the second image share a single disk.

The input interface 130 is configured to receive instructions from the operator and to forward the received instructions to the UI controlling circuitry 205. The UI controlling circuitry 205 is configured to receive an instruction from the input interface 130 indicating that a motion artifact correcting process should be performed, and to cause the motion artifact correcting circuitry 220 to perform the motion artifact correcting process.

When the first image is to be displayed on the monitor 109, the motion artifact correcting circuitry 220 is configured to calculate a shift amount by using the second image and to correct the first image by using the calculated shift amount. In that situation, in the X-ray image acquirer 110a, a pixel shift on/off switch illustrated in FIG. 7 is moved to side "b" by the UI controlling circuitry 205 that has received a user command from the input interface 130. The motion artifact correcting circuitry 220 includes re-sizing coefficient storage circuitry 221, pixel shift amount calculating circuitry 222, pixel shift amount applying circuitry 223, image processing circuitry 224, and re-sizing circuitry 225.

The re-sizing coefficient storage circuitry 221 is configured to store therein coefficients corresponding to sizes of the FOV. The pixel shift amount calculating circuitry 222 is configured to calculate the shift amount by using the second image. For example, because the second FED image is also input to the X-ray image acquirer 110a at the same time, the pixel shift amount calculating circuitry 222 calculates a movement of the subject with a smaller pixel pitch and a higher level of precision, by using the second FED image. More specifically, the pixel shift amount calculating circuitry 222 calculates the shift amount by using the second image acquired at the time of the acquisition of the mask image and the second image obtained at the time of the acquisition of the contrast image.

The re-sizing circuitry 225 is configured to calculate the shift amount by making a correction by multiplying the pixel pitch of the second image by a coefficient corresponding to the size of the FOV. For example, the first image and the second image have mutually-different pixel pitches. For this reason, when a shift amount calculated by the pixel shift amount calculating circuitry 222 is applied to the first FPD image, it is necessary to correct the difference in the image size caused by the difference in the pixel pitch between the first image and the second image. Accordingly, the re-sizing circuitry 225 calculates the shift amount in which the difference in the pixel pitch has been corrected, by performing the multiplying process using the coefficient corresponding to the selected size of the FOV.

The pixel shift amount applying circuitry 223 applies the calculated shift amount to the first image. For example, the pixel shift amount applying circuitry 223 corrects either the mask image or the contrast image of the first image, by using the calculated shift amount. In this situation, although the size of the FOV in the first FPD image is larger than the size of the FOV of the second FPD, a value calculated for a center part may be used as the shift amount, and it is acceptable for the pixel shift amount applying circuitry 223 to apply the calculated shift amount to perimeter parts as well without any modification. Alternatively, it is also acceptable for the pixel shift amount applying circuitry 223 to approximate a shift amount on the outside of the FOV of the second FPD on the basis of shift amount transition characteristics obtained from an image center part within the FOV of the second FPD and to apply the approximated shift amount on the outside of the FOV of the second FPD to the first image.

The image processing circuitry 224 is configured to cause the monitor 109 to display images. For example, in the situation where the DSA manipulations are performed while the operator is looking at the first image, when the first image is to be displayed, the image processing circuitry 224 causes the monitor 109 to display the first image in which motion artifacts have been corrected by using the second image. When the second image is to be displayed, the image processing circuitry 224 reads the second image from the disk 203 and causes the monitor 109 to display the read second image.

Figure 8:
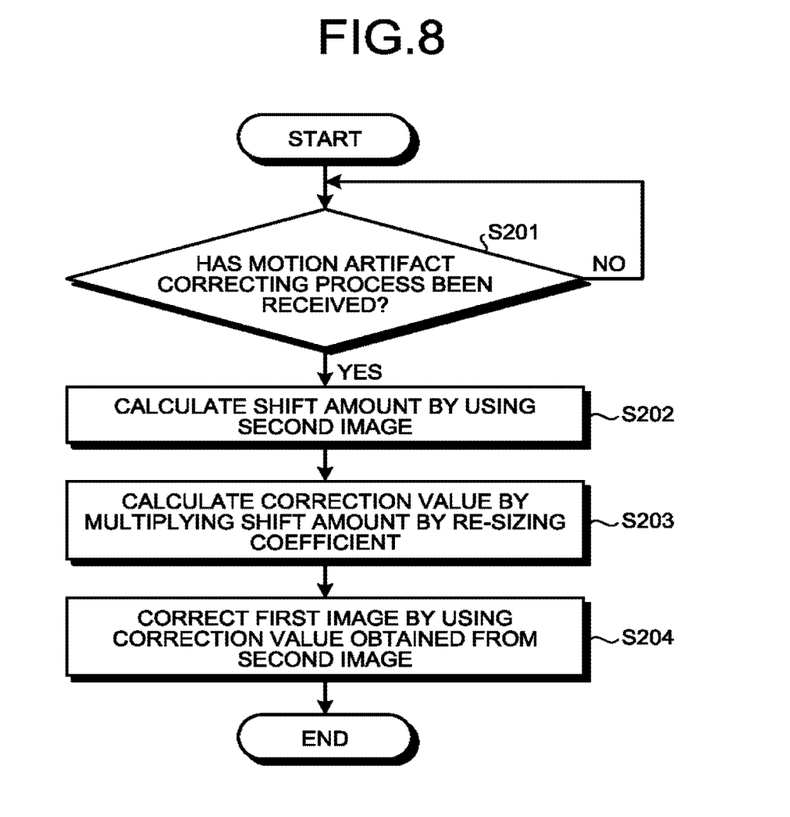
FIG. 8 is a flowchart illustrating a processing procedure performed by the X-ray image acquirer according to the second embodiment.

FIG. 8 is a flowchart illustrating a processing procedure performed by the X-ray image acquirer 110a according to the second embodiment. FIG. 8 presents the flowchart explaining overall operations of the X-ray image acquirer 110a, and the following sections will explain to which steps in the flowchart, the constituent elements thereof correspond. The procedure will be explained on the assumption that the processes illustrated in FIG. 8 are performed after the mask image and the contrast image are acquired through DSA manipulations.

Step S201 is a step implemented by the UI controlling circuitry 205. At step S201, the UI controlling circuitry 205 determines whether or not a motion artifact correcting process has been received. In this situation, when it is determined that no motion artifact correcting process has been received (step S201: No), the UI controlling circuitry 205 repeatedly performs the process at step S201. On the contrary, when it is determined that a motion artifact correcting process has been received (step S201: Yes), the UI controlling circuitry 205 proceeds to step S202.

Step S202 is a step implemented by the pixel shift amount calculating circuitry 222 included in the motion artifact correcting circuitry 220. At step S202, the pixel shift amount calculating circuitry 222 calculates a shift amount by using the second image.

Step S203 is a step implemented by the re-sizing circuitry 225 included in the motion artifact correcting circuitry 220. At step S203, the re-sizing circuitry 225 calculates a correction value by multiplying the shift amount by the re-sizing coefficient.

Step S204 is a step implemented by the pixel shift amount applying circuitry 223 included in the motion artifact correcting circuitry 220. At step S204, the pixel shift amount applying circuitry 223 corrects the first image by using the correction value obtained from the second image.

As explained above, in the second embodiment, the resolution of the second photodetector 106b is higher than that of the first photodetector 106a. In other words, the second photodetector 106b is able to more accurately calculate the pixel shift amount between the mask image and the contrast image. Further, in the second embodiment, when the first image is to be displayed on the monitor 109, the X-ray image acquirer 110a calculates the shift amount by using the second image and further corrects the first image by using the calculated shift amount. As a result, according to the second embodiment, for example, it is possible to provide a DSA image in which the motion artifact has been corrected with a higher level of precision.

In the second embodiment above, the example is explained in which the X-ray image acquirer 110a performs the process of correcting the motion artifacts, after the mask image and the contrast image are acquired through the DSA manipulations; however, embodiments are not limited to this example. For instance, the X-ray image acquirer 110a may perform the process of correcting the motion artifacts in real time, every time a contrast image is acquired.

Embodiments are not limited to the embodiments described above.

In the embodiments above, the example is explained in which, as illustrated in FIG. 4 or FIG. 7, in the X-ray detector 106, the first FED is provided on the X-ray source 103 side, relative to the second FED; however, embodiments are not limited to this example. For instance, in the X-ray detector 106, the second FPD may be provided on the X-ray source 103 side, relative to the first FED.

Further, in the embodiments above, the example is explained in which the X-ray image acquirer 110 (or 110a) includes the circuitry; however, embodiments are not limited to this example. For instance, another arrangement is acceptable in which the X-ray image acquirer 110 (or 110a) is a processor and, as a result of the processor reading and executing computer programs (hereinafter, "programs") stored in storage circuitry, the functions that are the same as those of the X-ray image acquirer 110 illustrated in FIG. 4 or the X-ray image acquirer 110a illustrated in FIG. 7 are executed. In that situation, the processing functions executed by the processor are recorded in the storage circuitry in the form of computer-executable programs. The processor implements the functions corresponding to the programs by reading the programs from the storage circuitry and executing the read programs. In other words, the processor that has read the programs has the functions that are the same as those of the circuitry illustrated within the X-ray image acquirer 110 in FIG. 4 or within the X-ray image acquirer 110a in FIG. 7.

The term "processor" used in the above explanation denotes, for example, a Central Processing Unit (CPU), a Graphics Processing Unit (GPU), or a circuit such as an Application Specific integrated Circuit (ASIC) or a programmable logic device (e.g., a Simple Programmable Logic Device [SPLD], a Complex Programmable Logic Device [CPLD], or a Field Programmable Gate Array [FPGA]). The processor implements the functions thereof by reading the programs stored in the storage circuitry and executing the read programs. Instead of storing the programs into the storage circuitry, it is also acceptable to directly incorporate the programs into the circuit of the processor. In that situation, the processor implements the functions thereof by reading the programs incorporated in the circuit thereof and executing the read programs. The processors disclosed in the embodiments do not each necessarily have to be structured as a single circuit. It is also acceptable to structure one processor by combining together a plurality of independent circuits so as to implement the functions thereof. Further, it is also acceptable to integrate two or more of the constituent elements illustrated in FIG. 4 or FIG. 7 into one processor so as to implement the functions thereof.

In the explanation of the embodiments above, the constituent elements of the apparatuses and the devices illustrated in the drawings in the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be implemented by a CPU and a computer program analyzed and executed by the CPU or may be implemented as hardware using wired logic.

It is possible to implement the controlling methods described in the embodiments above by causing a controlling program prepared in advance to be executed by a computer such as a personal computer, a workstation, or the like. The controlling program may be distributed via a network such as the Internet. Further, the controlling program may be recorded onto a computer-readable recording medium such as a hard disk, a flexible disk (FD), a Compact Disk Read-Only Memory (CD-ROM), a magneto-optical (MO) disk, a Digital Versatile Disk (DVD), or the like, so as to be executed as being read from the recording medium by a computer.

According to at least one aspect of the embodiments described above, it is possible to reduce the artifacts.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
    an X-ray detector including a first detector and a second detector capable of simultaneously detecting X-rays irradiated from an X-ray tube; and
    processing circuitry configured to correct, by using information of a second image that is based on an output from the second detector, a first image that is based on an output from the first detector.

2. The X-ray diagnostic apparatus according to claim 1, wherein
    the X-ray detector includes:

a scintillator configured to convert an X-ray into light; and a first photodetector and a second photodetector configured to share the scintillator and detect light converted by the scintillator, the first detector includes the scintillator and the first photodetector, the second detector includes the scintillator and the second photodetector, and the first photodetector and the second photodetector simultaneously detect light converted from X-rays by the scintillator.

3. The X-ray diagnostic apparatus according to claim 2, wherein the scintillator is arranged so as to be sandwiched between the first photodetector and the second photodetector.

4. The X-ray diagnostic apparatus according to claim 2, wherein a residual component resulting from incident X-ray of the second photodetector is smaller than that of the first photodetector, and in a situation where an artifact due to the residual component occurs in the first image, when an image displayed on a display is changed from the second image to the first image, the processing circuitry corrects the first image by using a pixel value obtained from the second image.

5. The X-ray diagnostic apparatus according to claim 4, wherein, when a difference between a pixel value obtained by multiplying a pixel value of the second image by a coefficient corresponding to a sensitivity ratio between the first photodetector and the second photodetector and a pixel value of the first image is equal to or larger than a threshold value, the processing circuitry determines that the artifact has occurred.

6. The X-ray diagnostic apparatus according to claim 5, wherein a resolution of the second photodetector is higher than that of the first photodetector, and when comparing a pixel value of the first image with a pixel value of the second image, the processing circuitry corrects a pixel pitch of the second image.

7. The X-ray diagnostic apparatus according to claim 4, wherein the processing circuitry calculates a correction value based on a pixel value obtained from the second image and a pixel value obtained from the first image, and further corrects the first image by subtracting the correction value from the pixel value obtained from the first image.

8. The X-ray diagnostic apparatus according to claim 7, wherein the processing circuitry corrects at least one of a pixel value obtained from the second image and a pixel value obtained from the first image corresponding to sensitivity of the first photodetector and the second photodetector, and further calculates a correction value by subtracting a pixel value obtained from the corrected first image from a pixel value obtained from the corrected second image.

9. The X-ray diagnostic apparatus according to claim wherein a resolution of the second photodetector is higher than that of the first photodetector, and when the first image is to be displayed on a display, the processing circuitry calculates a shift amount by using the second image and further corrects the first image by using the calculated shift amount.

10. The X-ray diagnostic apparatus according to claim 9, wherein the processing circuitry calculates the shift amount by making a correction by multiplying a pixel pitch of the second image by a coefficient corresponding to a size of a field of view.

11. The X-ray diagnostic apparatus according to claim 2, wherein a size of a field of view of the first photodetector is larger than that of the second photodetector.

* * * * *